(12) United States Patent
Strehl

(10) Patent No.: US 9,763,611 B2
(45) Date of Patent: Sep. 19, 2017

(54) LANCING DEVICE FOR OBTAINING SAMPLES OF BODY FLUID

(71) Applicant: Gerresheimer Regensburg GmbH, Regensburg (DE)

(72) Inventor: Michael Strehl, Pfreimd (DE)

(73) Assignee: Gerresheimer Regensburg GMBH, Regensburg (DE)

( * ) Notice: Subject to any disclaimer, the term of this patent is extended or adjusted under 35 U.S.C. 154(b) by 0 days.

(21) Appl. No.: 14/422,674

(22) PCT Filed: Jun. 18, 2013

(86) PCT No.: PCT/EP2013/062659
§ 371 (c)(1),
(2) Date: Jun. 7, 2015

(87) PCT Pub. No.: WO2014/029521
PCT Pub. Date: Feb. 27, 2014

(65) Prior Publication Data
US 2015/0265199 A1    Sep. 24, 2015

(30) Foreign Application Priority Data

Aug. 22, 2012 (DE) .................. 10 2012 107 749

(51) Int. Cl.
*A61B 5/15* (2006.01)
*A61B 5/151* (2006.01)

(52) U.S. Cl.
CPC .. *A61B 5/150641* (2013.01); *A61B 5/150022* (2013.01); *A61B 5/15113* (2013.01);
(Continued)

(58) Field of Classification Search
None
See application file for complete search history.

(56) References Cited

U.S. PATENT DOCUMENTS

| 7,875,243 B2 | 1/2011 | Rush et al. | |
| 2009/0281459 A1* | 11/2009 | Faulkner | A61B 5/15186 600/583 |
| 2010/0168616 A1* | 7/2010 | Schraga | A61B 5/1411 600/583 |

FOREIGN PATENT DOCUMENTS

| CN | 101076729 | 11/2007 |
| EP | 2198781 | 6/2010 |

(Continued)

OTHER PUBLICATIONS

Search Report, dated Oct. 1, 2013, corresponding to International Application No. PCT/EP2013/062659 (filed Jun. 18, 2013), 2 pp.
(Continued)

*Primary Examiner* — Devin Henson
*Assistant Examiner* — Benjamin Melhus
(74) *Attorney, Agent, or Firm* — Lathrop & Gage LLP

(57) ABSTRACT

The invention relates to a lancing device (1) for obtaining bodily fluid samples, comprising a base body (3), on one longitudinal-face end (6) of which a removable cap (12) is arranged which has a positioning face (8) with an outlet opening (7), a lancet magazine (4) for receiving at least one lancet (5), which is held replaceably in the base body (3), a drive device (14) for moving a lancet (5) arranged in the lancet magazine (4) back and forth in the direction of the longitudinal axis (2), said lancet being positioned therein in such a way that the tip thereof can exit the outlet opening (7) during the movement back and forth, wherein the lancet magazine (4) has a locking element (30) and the cap (12) has an unlocking element (31) formed to engage in the locking element (30).

11 Claims, 5 Drawing Sheets

Figure 1:
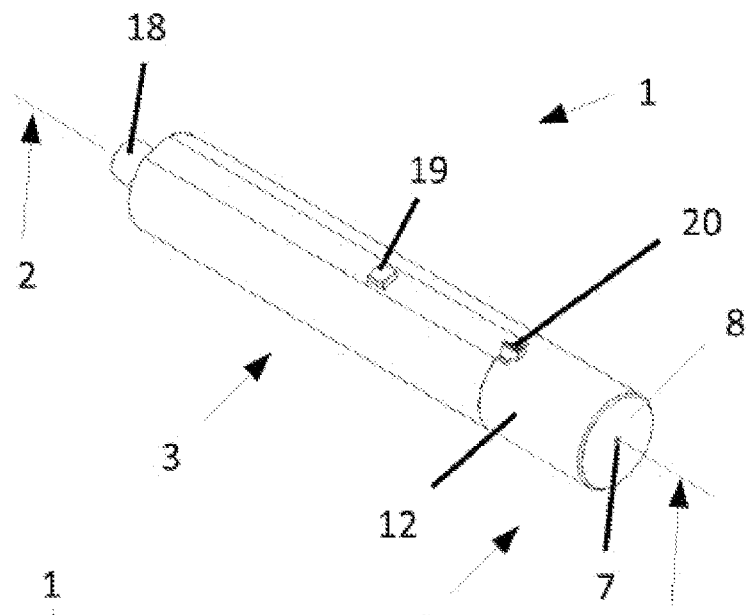

(52) U.S. Cl.
CPC ...... *A61B 5/15115* (2013.01); *A61B 5/15117* (2013.01); *A61B 5/15146* (2013.01); *A61B 5/15153* (2013.01); *A61B 5/15163* (2013.01); *A61B 5/15173* (2013.01); *A61B 5/150412* (2013.01); *A61B 5/150503* (2013.01); *A61B 5/150961* (2013.01); *A61B 5/1513* (2013.01); *A61B 5/15169* (2013.01); *A61B 5/150183* (2013.01)

(56) References Cited

FOREIGN PATENT DOCUMENTS

| JP | H06114039 | 4/1994 |
|----|-----------|--------|
| WO | 2006/065754 | 6/2006 |
| WO | WO 2007/069572 | 6/2007 |
| WO | 2008/064333 | 5/2008 |

OTHER PUBLICATIONS

First Office Action in Chinese Application No. 201380043682.8, a related application, dated Apr. 28, 2017, English translation.

\* cited by examiner

LANCING DEVICE FOR OBTAINING SAMPLES OF BODY FLUID

CROSS-REFERENCE TO RELATED APPLICATIONS

This application is a U.S. National Stage Application filed under 35 U.S.C. §371 of International Application No. PCT/EP2013/062659, filed Jun. 18, 2013, which claims the benefit of German Application No. 10 2012 107 749.5, filed Aug. 22, 2012. All of these applications are hereby incorporated by reference in their entireties.

The invention relates to a lancing device for obtaining bodily fluid samples according to the preamble of claim 1. The invention further relates to a lancet magazine for a lancing device of this type.

A lancing device of this type is already known from WO 2006/027255 A1. This lancing device has a lancet magazine in the form of a magazine drum in which the lancets, which can be inserted therein, are arranged in a rotationally symmetrical manner about an axis of rotation of the magazine drum and can be moved along a circular path. After a lancet magazine is laid in a lancing device of this type, the lancet magazine is generally further enclosed by a cap. In this respect, this cap generally contains means for adjusting the lancing depth. This regulation option should make it possible for the end user to set the optimum lancing depth of the needle or lancet respectively, taking into account the properties of his/her skin and if appropriate other personal physiological properties, in such a way that he/she can obtain a precisely sufficient amount of blood for the application with as little pain as possible.

WO 2008/064333 A2 discloses a lancing device comprising a base body, a lancet magazine, an adjustment device for the lancing depth and a removable cap. To use the lancing device, the lancet magazine has to be laid in the housing and be secured in the housing by snapping a locking element arranged on the lancet magazine into a groove provided therefore in the base body. After each lancing process, the magazine is further rotated about a discrete position in the housing so as to bring an as yet unused lancet into the lancing position. Only once all of the lancets have been used once and an end position is reached does the locking element engage in a conical face provided therefore on the housing, causing the lancet magazine to be unlocked and be removable from the housing. The removable cap contains an opening for the needle applied to the lancet. However, no unlocking element is provided on the cap.

If an end user loses this cap or forgets to place it on the magazine, the lancing devices are generally still functional, and can thus also be released. However, if the cap and the lancing depth adjustment system connected thereto are not used, the outer housing of the magazine is placed directly on the skin surface. The lancing depth of the needle therefore corresponds to the lancing depth originally set with the cap plus the wall thickness of the cap. This leads to deeper penetration of the needle or lancet respectively into the tissue of the end user, and this can sometimes be very painful and under some circumstances even dangerous, if for example larger blood vessels are accidentally pierced by the needle. To prevent this incorrect use, it is necessary to disable use of the lancing device without the cap provided therefore.

The object of the invention is therefore to further develop a lancing device in accordance with the preamble of claim 1 in such a way that use of the lancing device without the cap placed on the lancet magazine is effectively disabled.

This object is achieved by a lancing device having the features of claim 1. Advantageous configurations of the invention can be found in the dependent claims.

The lancing device according to the invention for obtaining bodily fluid samples basically shows the following:
a) a base body, which is substantially rotationally symmetrical about the longitudinal axis thereof, on one longitudinal-face end of which a removable cap is arranged which comprises a positioning face having an outlet opening,
b) a lancet magazine for receiving a plurality of lancets, which is held replaceably in the base body,
c) a drive device for moving a lancet arranged in the lancet magazine back and forth in the direction of the longitudinal axis, said lancet being positioned therein in such a way that the tip thereof can exit the outlet opening during the movement back and forth.

In this respect, it is provided that the lancet magazine comprises a locking element and the cap comprises an unlocking element formed to engage in the locking element.

For the further discussion, it should be noted in advance that in the following the terms "needles" and "lancets" include not only cylindrical metal, plastics material or ceramic elements or similar elements, but also planar, elongate metal, plastics material or ceramic elements or similar elements, which optionally comprise not only a tip but also at least one cutting edge and which are suitable for penetrating tissue to take samples of bodily fluids, in particular to take blood samples.

As the lancet magazine is supplied, and after the cap is removed, a locking element blocks the movement of the drive device or of the lancet respectively. In this respect, this locking element is integrated directly into the interior of the lancet magazine.

In this process, an unlocking element applied to the inner face of the cap engages in the lancet magazine in such a way that the blocking locking element is moved away from the locking position thereof by the unlocking element and clears the displacement path for the movement of the drive device or of the lancet respectively. The locking element positioned in this manner thus no longer blocks the movement of the drive device or of the lancet respectively, in such a way that the lancet can be displaced by the drive device and the end user can carry out the lancing process.

Because of the lancing device according to the invention, it is now possible to avoid painful and/or dangerous lancing processes where the cap is not applied to the lancing device. Simple and comfortable handling is thus made possible for the user of the lancing device according to the invention. The invention effectively protects against undesirable painful and/or dangerous punctures when the lancing device is used, since the user can no longer initiate a lancing process when the cap is not applied to the lancing device.

According to a first advantageous configuration of the invention, the locking element is positioned flat on a locking tab in a locking position, and the two side regions thereof are braced on bracing elements of the drive device and of the lancet magazine. As a result of this configuration of the invention, movement of the drive device is disabled in a simple manner, since the displacement path of the drive device along or respectively parallel to the longitudinal axis of the base body is blocked by the locking element, which is braced on the bracing elements of the drive device and of the lancet magazine, and therefore no lancing processes can be initiated.

In this context, it has been found to be advantageous that, upon engaging in the locking element, the unlocking element transfers said locking element into an unlocked position, in which the locking element is raised from the locking tab and the side regions thereof are disengaged from at least one of the bracing elements of the drive device and of the lancet magazine. As a result, displacement of the drive device along or respectively parallel to the longitudinal axis of the base body is now possible again. Lancing processes can therefore be carried out by the user without difficulty once the cap is placed on the lancing device. According to a further concept of the invention, the locking element is in the form of a spring element, in particular a leaf spring element, and the unlocking element is in the form of a pin. As a result of this configuration, the spring element is raised from the locking tab, while building up a restoring force, once the pin comes into engagement with the spring element. Movement of the drive device along or parallel to the longitudinal axis of the base body respectively is thus made possible. If the cap is removed from the lancing device again, the previously built-up restoring force of the spring is dissipated again, the spring being laid down on the locking tab again and the side regions thereof being braced on the bracing faces of the drive device and of the lancet magazine.

To make it easier to raise the leaf spring element from the locking tab, it has been found to be advantageous for the leaf spring element and the pin to show mutually adapted ramp slopes. These ramp slopes slide on one another when the cap is placed on the lancing device, and thus make it easier to raise the leaf spring element from the locking tab and thus to release the displacement path for the movement of the drive device or of the lancet respectively along or respectively parallel to the longitudinal axis of the base body.

For the interior of the lancet magazine and thus the lancets to be protected from soiling and contamination, an outer magazine housing is provided for the lancet magazine, which comprises an outlet opening corresponding to the outlet opening of the cap. As a result, the lancets, which are generally produced sterile, are kept safely in the lancet magazine, it being possible to move the tips thereof through the outlet openings of the lancet magazine and the cap by means of the drive device. Lancing processes can therefore be carried out in a simple manner, the lancets also being received safely in the magazine housing again after use, in such a way that any third parties who for example dispose of used lancets or lancet magazines respectively cannot come into contact with the used lancets, to which blood constituents or other bodily fluids which pose a risk of infection could possibly adhere.

Further, the lancet magazine is placed on a magazine housing cover, which can be connected to the magazine housing, for example using snap-in hooks, the magazine housing cover comprising an opening for the engagement of the drive device, in such a way that the entire lancet magazine is encapsulated apart from the outlet opening for the lancet, the opening for the pin of the cap and an opening for the engagement of the drive device.

To further reduce the risk of infection, the outer magazine housing comprises an end face, which contains the outlet opening for the lancet as well as an opening for the unlocking element of the cap and forms the bracing element of the lancet magazine. As a result of this configuration of the invention, the entire lancet magazine is encapsulated apart from the outlet opening for the lancet, the opening for the pin of the cap and an opening for the engagement of the drive device. This further results in a reduction in components, since no separate bracing element for the locking element is provided for the lancet magazine because the end face also takes on the function of a bracing element of this type.

According to a further concept of the invention, the drive device has a drive plunger and a release plunger, which can be coupled to and decoupled from a needle of whichever lancet is positioned in such a way that the tip thereof can exit the outlet opening of the cap during the movement back and forth. Advantageously, in this respect, the drive plunger is releasably connectable to the release plunger, it being possible to provide that the drive plunger is assigned to the base body of the lancing device and the release plunger is assigned to the lancet magazine. Thus, each lancet magazine to be used is provided with its own release plunger, which is releasably connectable to the drive plunger of the base body of the lancing device. This measure also circumvents possible infection risks, since the release plunger has direct contact with the lancets and the possibility thus it cannot be excluded that blood adhering to the used lancets or other bodily fluids may arrive on the release plunger in liquid form or else, after drying, in solid form. Therefore, with each new lancet magazine a new release plunger is also used every time.

For the displacement back and forth, the drive device is for example spring-loadable. The base body therefore comprises a tensioning element for tensioning the drive device, in particular under a spring load, and a trigger element for slackening the drive device. Of course, it is also possible to provide the drive device with a motor, in particular an electric motor. However, spring loading is preferred for this purpose, since it guarantees a short dwell time of the tip of the needle of the lancet in the puncture site and thus minimises the lancing time and thus the potential lancing pain for the user.

In a further advantageous configuration of the invention, a clock device is provided, which is designed to move the lancet which is positioned in such a way that the tip thereof can exit the outlet opening during the movement back and forth out of the position thereof in the guidance path of the lancet magazine and to move an adjacent lancet into this position. This ensures that each lancet located in the lancet magazine is only used once. Residues of bodily fluids, in particular blood, generally still adhere to the needle tip of a used lancet, which pose a risk of infection for further users of the same lancing device if they are not moved out of the position for the movement back and forth of the needle of the lancet. A potential risk of infection is thus further reduced by this measure. However, to prevent used lancets from rotating continuously in the lancet magazine and possibly also being reused unintentionally by a user, a stop device having a locking function may be provided within the lancet magazine, making it necessary to remove the lancet magazine when each lancet within the lancet magazine has been used once.

The clock device may be formed to be manually operable by means of a clock trigger element. However, it is also possible to form the clock device in such a way that it repositions the lancets automatically, preferably by way of a spring mechanism or an electric motor.

The invention also independently protects a lancet magazine and a cap, as disclosed in greater detail previously above, for use in an above-disclosed lancing device.

Further aims, advantages, features and possible applications of the present invention may be seen from the following description of embodiments with reference to the drawings. In this context, all of the features which are described and/or shown in the drawings, in isolation or in any reasonable combination, form the subject matter of the present invention, also irrespective of how they are compiled in the claims or the dependencies thereof.

Figure 2:
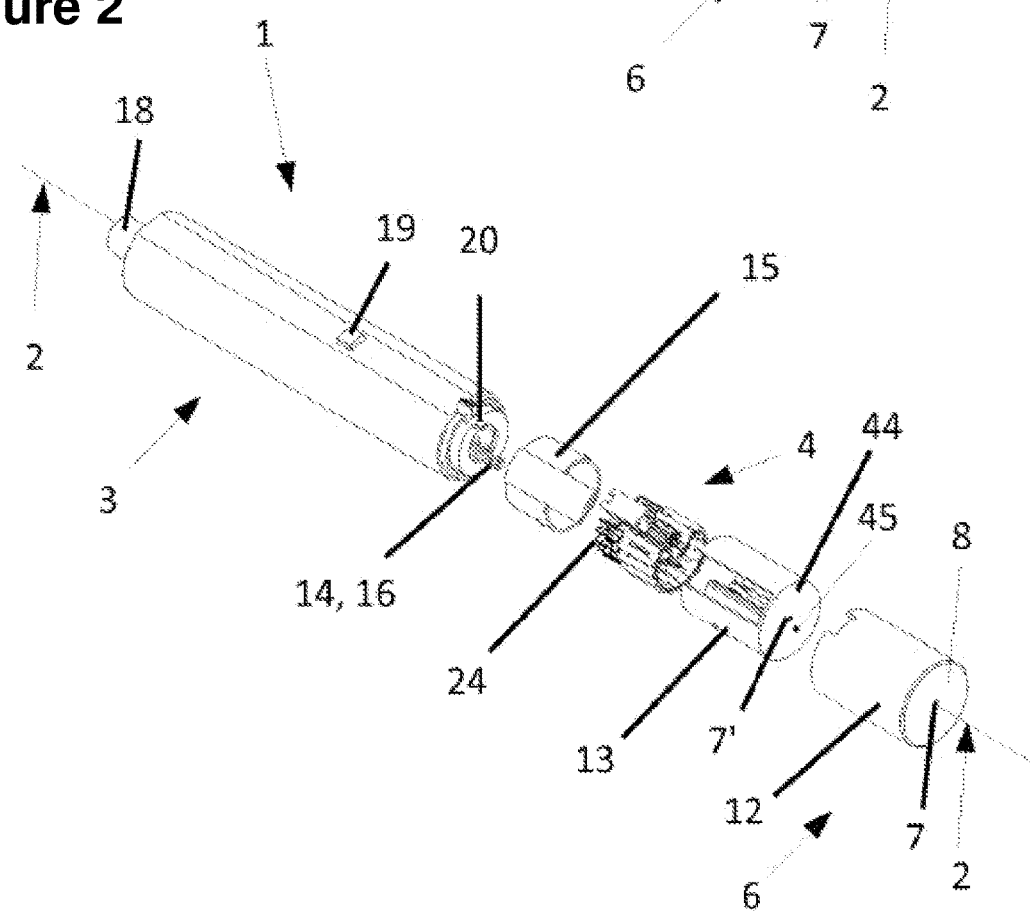
Figure 3:
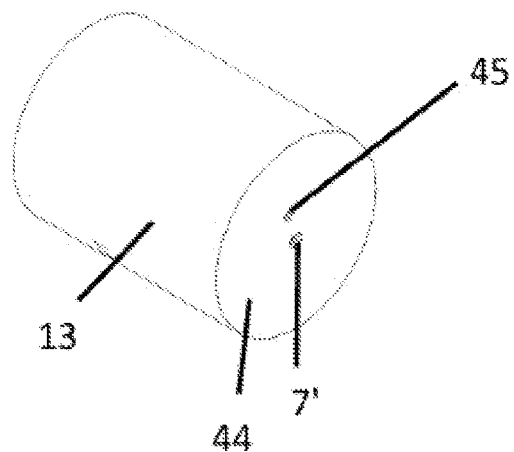
Figure 4:
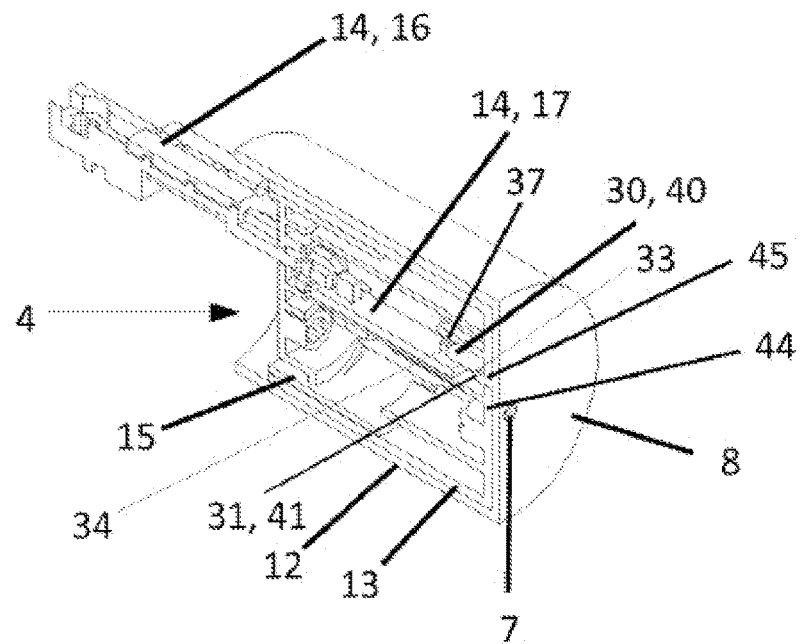
Figure 5:
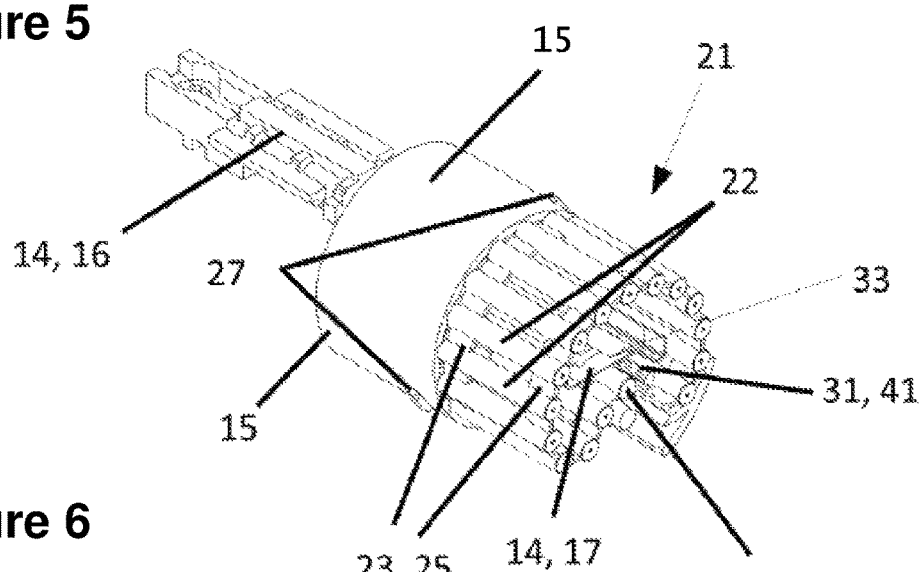
Figure 6:
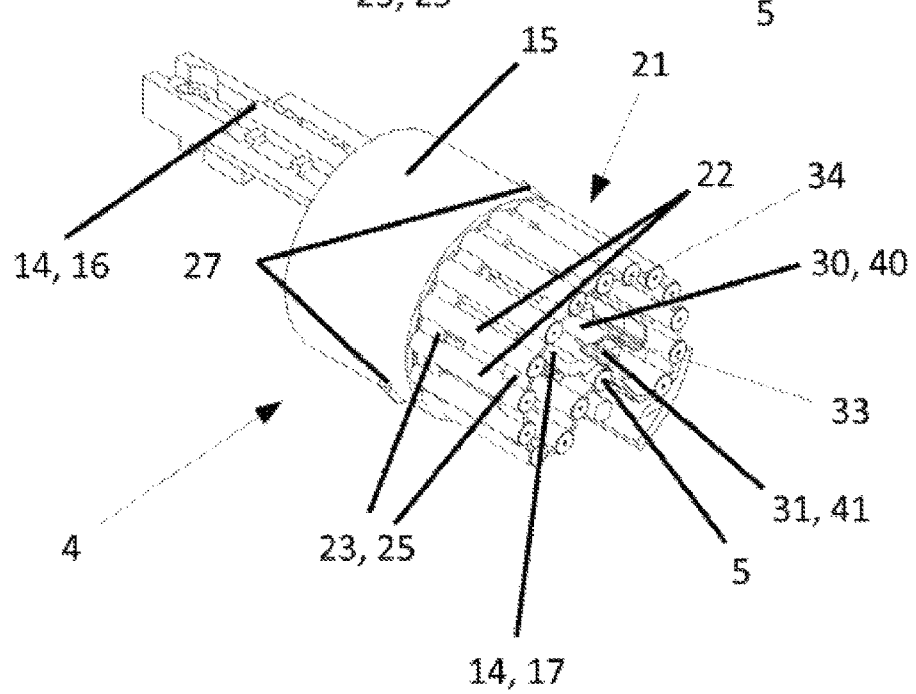
Figure 7:
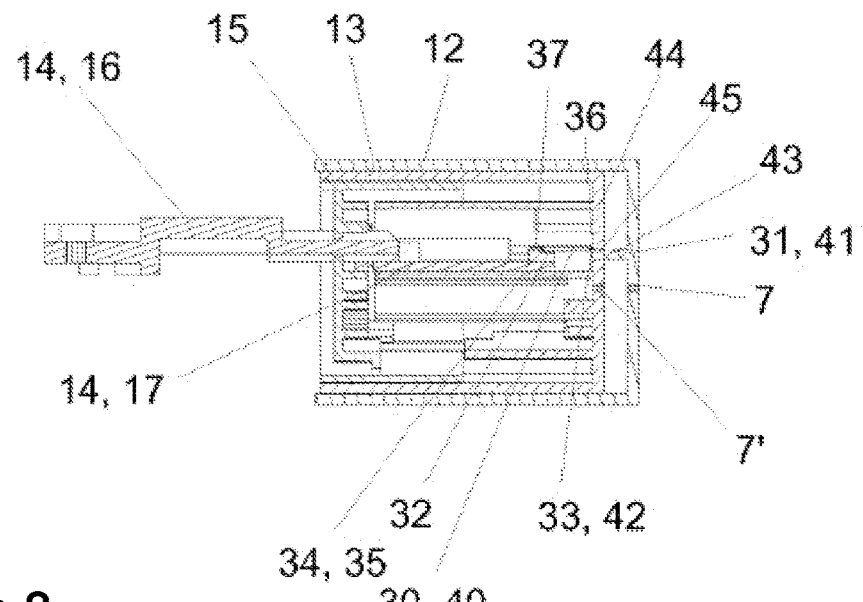
Figure 8:
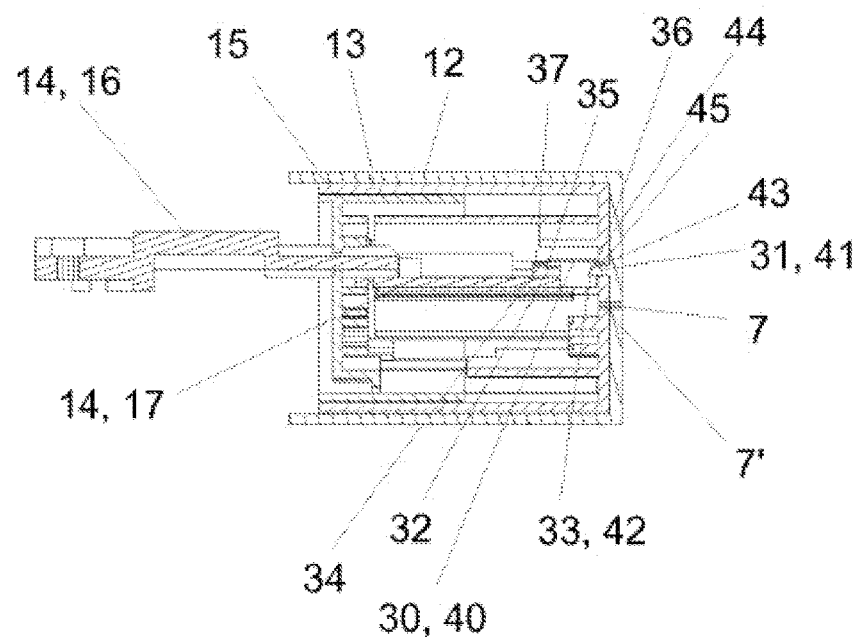
Figure 9:
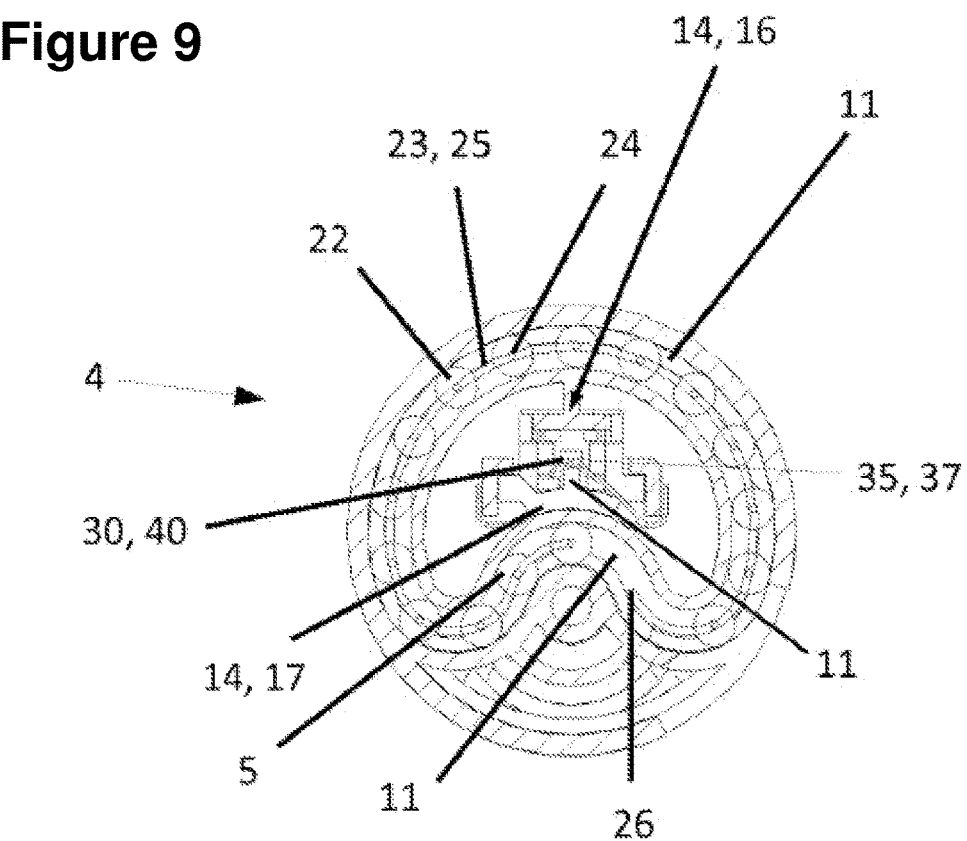
Figure 10:
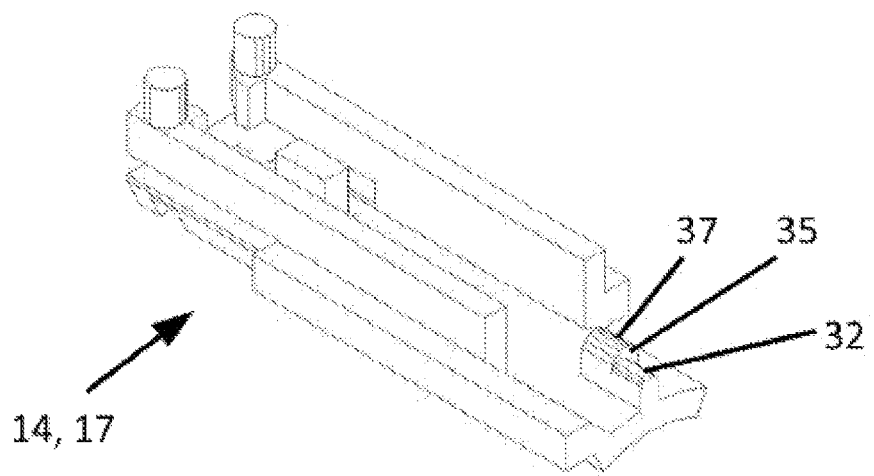

In the drawings:

FIG. 1 is a perspective view of an embodiment of a lancing device according to the invention when closed, FIG. 2 is an exploded view of the lancing device of FIG. 1, FIG. 3 is a perspective view of an outer magazine housing of the lancing device according to FIGS. 1 and 2, FIG. 4 is a sectional view of the outer magazine housing of FIG. 3, in which a drive unit comprising a drive plunger and a release plunger engages in the lancet magazine, FIG. 5 is a perspective view of an embodiment of a lancet magazine of a lancing device according to the invention comprising a locking element located in a first position, having an inserted lancet band, FIG. 6 is a perspective view of the lancet magazine of FIG. 5, having a locking element located in a second position, FIG. 7 is a sectional view of the lancet magazine of FIG. 5, the lancet magazine being placed in a magazine cover and being enclosed by an outer magazine housing and covered by a cap, FIG. 8 is a sectional view of the lancet magazine of FIG. 6, the lancet magazine being placed in a magazine cover and being enclosed by an outer magazine housing and covered by a cap, FIG. 9 is a cross-section of the lancet magazine of FIG. 5 from the front, perpendicular to a longitudinal axis, and FIG. 10 is a perspective view of an embodiment of a release plunger for a lancing device according to the invention.

FIG. 1 shows an embodiment of a lancing device 1 according to the invention. This lancing device 1 is formed substantially rotationally symmetrically about a longitudinal axis 2 of a base body 3 of the lancing device 1. On one end 6, the base body has a cap 12, by means of which a lancet magazine 4, arranged in the interior of the lancing device 1 or of the base body 3, can be covered. Further, this cap 12 also has means (not shown in the drawings) for adjusting the lancing depth of the needle 24.

The lancing device 1 is provided with a drive device 14 (not shown in greater detail in the drawings), by means of which a needle 24 of a lancet 5 located in the lancet magazine 4 can be moved out through the outlet opening 7 and also moved back into the lancing device 1, by spring loading.

For the drive device 14 to be able to move a needle 24 back and forth, a trigger element 19, by means of which a one-time movement back and forth of the needle 24 can be triggered, is provided on the base body 3 of the lancing device 1. However, a movement back and forth of this type of the needle 24 can only be initiated if the spring-loading of the drive device 14 has previously taken place. For this purpose, a tensioning element 18 is provided on the end of the lancing device 1 or base body 3 opposite the end 6, the drive device being loaded with a spring force when said tensioning element is actuated.

Further, an additional clock trigger element 20 for a clock device (not shown in greater detail in the drawings) is arranged on the base body 3. This clock trigger element 20 serves to initiate a movement of a lancet 5, which has been used once, within the guidance path 11 of the lancet magazine 4 after the lancet 5 has been moved by means of the drive device 14, in such a way that the tip of the needle 24 has exited through the outlet opening 7 and subsequently the needle 24 has been pulled back completely into the lancing device 1. The movement initiated by the clock trigger element 20 takes place in such a way that the lancet 5 in the guidance path 11 is conveyed out of the original position thereof in the lancet magazine 4 and an adjacent lancet 5 is moved into this position, in such a way that this lancet 5 can now be displaced back and forth by the drive device 14.

FIG. 2 is an exploded view of the lancing device 1 of FIG. 1, such that the parts in the interior of the lancing device can also be seen. The drive plunger 16 of a drive device 14, which is in an operative connection with the trigger element 19 and the tensioning element 18, projects out of the base body 3 of the lancing device 1, on which the tensioning element 18 as well as the trigger element 19 and the clock trigger element 20 are arranged. When the lancing device 1 is closed, this drive plunger 16 is in an operative connection with a release plunger 17 for a needle 24 or a lancet 5 respectively, which is positioned in the lancet magazine 4 in such a way that the tip thereof can exit through an outlet opening 7 on the positioning face 8. As is shown in particular in FIG. 2, both an outer magazine housing 13 and an outer magazine housing cover 15 are provided for the lancet magazine 4. The lancet magazine 4 can be received so as to be substantially encapsulated therein, in such a way that the lancets 5 located in the lancet magazine 4 are substantially protected from external influences and thus from soiling and contamination, even when the cap 12 is not applied to the lancing device 1. In this respect, an end face 44 of the outer magazine housing 13 comprises an outlet opening 7', which is brought to coincide with the outlet opening 7 of the cap 12 when the cap 12 is placed on the lancing device 1 or on the base body 3 thereof respectively. A needle 24, correspondingly positioned inside a lancet magazine 4 arranged in the lancing device 1 or the lancet 5 respectively can thus be moved out through the two outlet openings 7 and 7' and thus carry out a lancing process.

This end face 44 further comprises a further opening 45, through which an unlocking element 31 arranged on the cap 12 can engage in the lancet magazine 4, so as to move a locking element 30 out of a locking position, in which the drive device 14 is prevented from moving the lancet 5 or the needle 24 respectively along or respectively parallel to the longitudinal axis 2, into an unlocked position, in which the drive device 14 can move the lancet 5 or the needle 24 respectively along the longitudinal axis 2 or parallel thereto.

FIG. 3 is a detail of the outer housing 13, in which the end face 44 and the outlet opening 7' formed therein for the needle 24 or the lancet 5 respectively and the opening 45 for the unlocking element 31 arranged on the cap 12 can be seen clearly.

FIG. 4 is a sectional view of the outer magazine housing 13 of FIG. 3, in which a drive unit 14 comprising a drive plunger 16 and a release plunger 17 engages in the lancet magazine 4, the cap 12 being applied to the outer magazine housing 13 and the outer magazine housing being connected to a magazine cover 15. In this respect, within the lancet magazine 4, the locking element 30 in the form of a leaf spring element 40 can be seen, which is located in this case in the unlocked position. This can be seen from the fact that the cap 12 is placed on the outer magazine housing 13, and the unlocking element 31 thereof in the form of a pin 41 holds the locking element 30 or leaf spring element 40 respectively in the unlocked position.

When the leaf spring element 40 is located in this unlocked position, a locking tab 32 and an unlocking tab 37 of the release plunger 17 of the drive device 14 can pass through under the leaf spring 40, as can be seen in particular in FIG. 8, in such a way that the tip of a needle 24 or lancet 5 respectively located in the lancet magazine 4 can be moved through the outlet openings 7, 7' of the positioning face 8 of the cap 12 and the end face 44 of the lancet magazine 4, by means of the drive device 14 as well as the drive plunger 16 and release plunger 17.

By contrast, FIG. 7 shows the locking position of the locking element 30 in the form of a leaf spring element 40. This element is positioned in this case on a support face of the locking tab 32 and the side regions 33 and 34 thereof are braced both on a bracing face 35 of the drive device 14 or the release plunger 17 respectively and on a bracing face 36 of the lancet magazine 4. In this respect, the bracing face 36 is formed by the end face 44 of the outer magazine housing 13 of the lancet magazine 4, and the bracing face 35 of the drive device 14 is formed by the step between the unlocking tab 37 and the locking tab 32. The leaf spring element 40 takes on this unlocked position precisely when the cap 12 is not placed or, as shown in FIG. 7, not completely placed on the outer magazine housing 13 of the lancet magazine 4.

If the cap 12 is now transferred from the position shown in FIG. 7 to the position of FIG. 8, the unlocking element 31, arranged on the cap 12 and in the form of a pin 41, is consequently passed through the opening 45 in the end face 44 of the outer magazine housing 13. A ramp slope 43 of the pin 41 thus slides on a ramp slope 42 of the locking element 30 in the form of a leaf spring element 40, and thus moves the leaf spring element 40 from the locking position thereof in accordance with FIG. 7 into the unlocked position of FIG. 8.

In the unlocked position, the side regions 33 and 34 of the leaf spring element 40 are no longer braced on the two bracing faces 35 and 36. Instead, only the side region 33 is still braced on the bracing face 36, whilst the side region 34 is positioned out of engagement with the bracing face 35. The drive device 14 can now pass the unlocking tab 32 of the release plunger 17 through under the leaf spring element 40 and thus carry out a lancing process.

If the cap 12 is now removed from the lancing device 1 or the outer housing 13 of the lancet magazine 4 respectively again, the spring-loaded leaf spring element 40 falls back onto the support face of the locking tab 32, in such a way that the locking position is now taken on again, and movement of the drive device 14 along with the drive- and release plungers 16, 17 in the direction of the end face 44, and thus also movement of the tip of a lancet 5 or needle 24 correspondingly positioned in the lancet magazine 4 through the outlet openings 7, 7', is not possible.

FIGS. 5 and 6 show the positioning of a lancet magazine 4 on an outer magazine housing cover 15 according to FIGS. 7 and 8. In this view, snap-in hooks 27 can also be seen, by means of which the outer magazine housing 13 can be fixed to the outer magazine housing cover 15. These drawings further show the unlocking element 31 in the form of a pin 41, which is arranged on the cap 12 (not shown here), since the interior of the lancet magazine 4 is to be shown in the locking position of FIG. 5 and the unlocked position of FIG. 6. In these drawings, a lancet band 21 comprising a plurality of lancets 5 is inserted into the lancet magazine 4. For clarity, however, here only one respective lancet 5 is provided with a reference numeral. In this respect, the lancets 5 are held displaceably in lancet bodies 22, which are connected by means of a connecting band 23 or by means of connecting webs 25 respectively.

FIG. 9 is a cross-section of the lancet magazine 4 according to FIG. 5 from the front, the locking element 30 in the form of a leaf spring element 40 again being located in the locking position thereof. An open lancet band 21 is inserted into the lancet magazine 4, which is guided in a guidance path 11. As a result of the guidance path, it is possible to position a lancet 5 of the lancet band 22 in such a way that the tip of the needle 24 or the lancet 5 respectively exits the outlet opening 7, 7' and can take on the lancing position. Restricted guidance of the lancets 5 within the guidance path 11 can also be seen clearly in this drawing, as can the engagement of the drive plunger 16 and release plunger 17 of the drive device 14 in the lancet magazine 4.

Finally, FIG. 10 shows the special configuration of the release plunger 17 with the unlocking tab 37 arranged thereon and the locking tab 32 on which the locking element 30 in the form of a leaf spring element 40 can be set down in the locking position thereof. Further, the bracing face 35 of the drive device 14 or of the release plunger 17 respectively for the side region 34 of the leaf spring element 40 can be seen clearly here.

LIST OF REFERENCE NUMERALS

1 Lancing device
2 Longitudinal axis
3 Base body
4 Lancet magazine
5 Lancet
6 Longitudinal-face end
7 Outlet opening
7' Outlet opening
8 Positioning face
11 Guidance path
12 Cap
13 Outer magazine housing
14 Drive device
15 Outer magazine housing cover
16 Drive plunger
17 Release plunger
18 Tensioning element
19 Trigger element
20 Clock trigger element
21 Lancet band
22 Lancet body
23 Connection band
24 Needle
25 Connecting webs
26 Lancet band end
27 Snap-in hooks
28 Needle end
30 Locking element
31 Unlocking element
32 Locking tab
33 Side region
34 Side region
35 Bracing element
36 Bracing element
37 Unlocking tab
40 Leaf spring
41 Pin
42 Ramp slope
43 Ramp slope
44 End face
45 Opening

The invention claimed is:

1. A lancing device for obtaining bodily fluid samples, comprising
   a) a base body, which is rotationally symmetrical about the longitudinal axis thereof, on one longitudinal-face end of which a removable cap is arranged which has a positioning face with a first outlet opening, b) a lancet magazine for receiving at least one lancet, which is held replaceably in the base body, c) a drive device for moving a lancet arranged in the lancet magazine back and forth in the direction of the longitudinal axis, said lancet being positioned therein in such a way that the tip thereof can exit the first outlet opening during the movement back and forth, wherein the lancet magazine has a locking element and the cap has an unlocking element formed to engage in the locking element, wherein the locking element is positioned flat on a locking tab in a locking position, and two side regions of the locking element are braced on bracing elements of the drive device and of the lancet magazine, and wherein upon engaging in the locking element, the unlocking element transfers said locking element into an unlocked position, in which the locking element is raised from the locking tab and the side regions of the locking element are disengaged from at least one of the bracing elements of the drive device and of the lancet magazine.

2. The lancing device according to claim 1, wherein the locking element is in the form of a spring element and the unlocking element is in the form of a pin.

3. The lancing device according to claim 2, wherein the spring element and the pin comprise mutually adapted ramp slopes.

4. The lancing device according to claim 2, wherein the locking element is in the form of a leaf spring element.

5. The lancing device according to claim 1, wherein an outer magazine housing is provided for the lancet magazine, which comprises a second outlet opening corresponding to the first outlet opening.

6. The lancing device according to claim 5, wherein the outer magazine housing comprises an end face, which contains the second outlet opening and an opening for the unlocking element of the cap and forms the bracing element of the lancet magazine.

7. The lancing device according to claim 1, wherein the drive device comprises a drive plunger and a release plunger, which can be coupled to and decoupled from a needle of whichever lancet is positioned in such a way that the tip thereof can exit the first outlet opening during the movement back and forth.

8. The lancing device according to claim 1, wherein the base body has a tensioning element for tensioning the drive device and a trigger element for slackening the drive device.

9. The lancing device according to claim 1, wherein a clock device is provided, which is formed to move the lancet, which is positioned in such a way that the tip thereof can exit the first outlet opening during the movement back and forth, out of a position of the lancet in a guidance path of the lancet magazine and to move an adjacent lancet into a position in a guidance path of the lancet magazine.

10. The lancing device according to claim 9, wherein the clock device is formed to be manually operable by means of a clock trigger element or the clock device is formed in such a way that it repositions the lancets automatically.

11. The lancing device according to claim 10, wherein the clock device repositions the lancets by way of a spring mechanism or an electric motor.

* * * * *